United States Patent
Turri (10) Patent No.: US 6,739,872 B1
(45) Date of Patent: May 25, 2004

(54) SECURITY DEVICE COMPRISING A STOP MEMBER FOR DRILLING INSTRUMENT USED IN PARTICULAR IN DENTAL SURGERY AND DEVICE PRE-CALIBRATING AND STORING DRILLING DEPTH

(75) Inventor: Achille Turri, Morbio Inferiore (CH)

(73) Assignee: Arsline SA, Vacallo (CH)

( * ) Notice: Subject to any disclaimer, the term of this patent is extended or adjusted under 35 U.S.C. 154(b) by 38 days.

(21) Appl. No.: 09/980,335

(22) PCT Filed: Jun. 2, 2000

(86) PCT No.: PCT/CH00/00309

§ 371 (c)(1),
(2), (4) Date: Mar. 15, 2002

(87) PCT Pub. No.: WO00/74585

PCT Pub. Date: Dec. 14, 2000

(30) Foreign Application Priority Data

Jun. 3, 1999 (CH) .............................................. 1043/99

(51) Int. Cl.⁷ .............................. A61C 3/00; B23B 51/00
(52) U.S. Cl. .......................... 433/75; 433/165; 408/202
(58) Field of Search ............................. 433/72, 75, 76, 433/165; 408/241.5, 202, 112, 10, 11, 12

(56) References Cited

U.S. PATENT DOCUMENTS

| | | | | |
|---|---|---|---|---|
| 569,896 A | * | 10/1896 | Van Cauwenberg | 408/202 |
| 3,562,913 A | * | 2/1971 | Saffro | 433/75 |
| 4,165,562 A | * | 8/1979 | Sarfatti | 433/75 |
| 4,526,542 A | * | 7/1985 | Kochis | 433/165 |
| 4,710,075 A | * | 12/1987 | Davison | 408/202 |
| 5,051,043 A | * | 9/1991 | Spitznagel | 408/72 R |
| 5,382,120 A | * | 1/1995 | Parsons | 408/16 |
| 5,746,551 A | * | 5/1998 | Skaggs | 408/1 R |

* cited by examiner

Primary Examiner—Todd E. Manahan
(74) Attorney, Agent, or Firm—Young & Thompson (57) ABSTRACT

A security device includes a stop member for a rotary drilling instrument used in particular in dental surgery. The stop member is capable of being positioned at a desired depth of drilling and of preventing the depth from being exceeded. The two elements drilling instrument and the stop member include coupling elements directly or indirectly linking them together and co-operating elements capable of transforming their movement, such that when the device is operating, the drilling instrument is retracted rearwards relative to the drilling direction and to the position of the stop member under the action of the elements when the front part of the stop member comes in contact with a neighboring surface. The co-operating elements preferably consist of a screw-nut system, the direction of the thread(s) of the system and the rotating direction of the drill being opposite. A device comprising a gauge containing a piston enables to pre-calibrate and store the desired drilling depth.

11 Claims, 5 Drawing Sheets

SECURITY DEVICE COMPRISING A STOP MEMBER FOR DRILLING INSTRUMENT USED IN PARTICULAR IN DENTAL SURGERY AND DEVICE PRE-CALIBRATING AND STORING DRILLING DEPTH

BACKGROUND OF THE INVENTION

The invention relates to a safety device comprising a stop for a drilling instrument of use inter alia in dental surgery. The invention also relates to a device for precalibrating and storing the depth of drilling and directly related to an advantageous process of using the safety device.

One preferred application of these devices is to dental implantology.

As is known, during some operations, inter alia the treatment of root canals, some dental lesions, hard dental or maxillary tissue (e.g. when fitting a dental implant) the depth of penetration, drilling or boring by a specific instrument (endodontic instrument, dental bur or drill, implantology drill bit, etc) must be to a clearly defined depth determined by the practitioner as required by the patient.

The defined depth must be actually obtained but not exceeded. This condition is particularly important in dental implantology, where it is essential to ensure the long-term reliability of the infrastructure for inserting into the jawbone in order to hold a fixed dental prosthesis, but without any risk of injury to neighbouring structures.

For these reasons, manufacturers propose various devices for conforming to these constraints.

Figure 1:
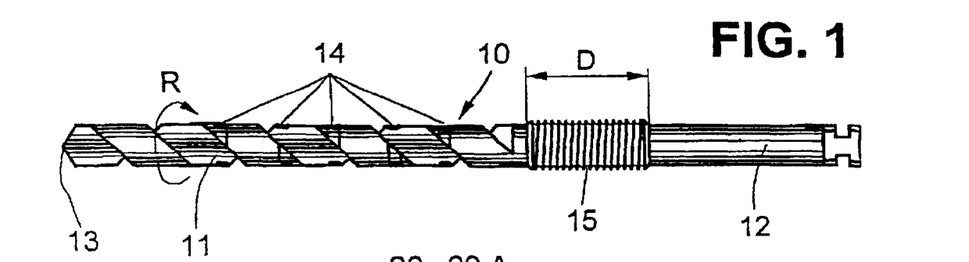
FIG. 1 represents a drill bit having a threaded shank.

For example, in a very simple but very frequently-used device in dental implantology, the instrument has markings in the form of grooves, coloured or otherwise, at different distances $P_1, P_2, \ldots P_n$ on the active part, i.e. the cutting part of the drill bit, so that the drilling operation can be stopped at the right moment, when the practitioner sees that the previously-determined depth has been reached (visual marks, reference 14 in the accompanying FIG. 1).

In other more sophisticated devices (which will be briefly described hereinafter) the instruments are provided with stops, although it should be noted that not one of these prior-art devices is suitable for dental implantology nor intended for use in this special sector.

EP-0 515 274 describes an instrument (a helical drill bit) used in dental surgery and having a cutting part 7 formed with transverse grooves which can serve as an optical reference part indicating the depth of drilling. The practitioner can place a stop ring (8, 9) on the appropriate groove, i.e. the groove corresponding to the depth of the hole which he intends to make, so that he will be better able to check the depth of drilling by positioning the stop, which will thus remain fixed during the required operation.

The teaching in FR-2 613 212 is similar except that the non-operative part 1b has a number of peripheral transverse notches for positioning a clip constituting a fixed depth stop for determining and checking the length of that part of the instrument which is to penetrate into the tooth.

In a variant disclosed in U.S. Pat. No. 4,526,542, the stop is screwed to the drill shank until locked against the rear surface of the cutting part, the screwthread or internal screwthread being oriented oppositely to the rotation of the drill, so that the stop serves as a lock-nut. When the stop comes in contact with a neighbouring surface it will tend to be locked more tightly on to the shoulder presented by the working part at the top. As we shall see hereinafter, this is contrary to the aim of the inventor of the present invention.

The International Application WO 98/03125 discloses a drill bit having a working part formed with calibrated recesses spaced apart (relative to the drill axis) by a millimeter in each case. An annular stop can be moved along the said working part and can be immobilised at each recess, when a pin disposed in the stop can engage in a recess under the action of a spring.

These devices can display the depth of drilling or boring intended by the practitioner, i.e. the stop on the instrument can be positioned in dependence on the said depth, and also serves as a safety element since the aim, once the instrument has been adjusted, is to ensure that the said depth is not exceeded during the operation.

All these known stop devices, however, have at least three kinds of disadvantages as regards the specialist in dental implantology who wishes to drill for the purpose of fitting implants. Firstly, insofar as a stop is simply fixed at a predetermined working position, the prior art devices to not always make optimum use of the depth of the site of operation, apart from the fact that the accuracy of depth display is unsatisfactory. Secondly, in cases where the working conditions are not optimum, these devices may produce an oval hole and thus endanger the primary stability of the implant, in which case a satisfactory result cannot be guaranteed, particularly as regards the stability of the implant (see hereinafter). Finally the prior art devices are uneconomic.

Although these three groups of disadvantages can easily be understood by examining the prior publications, it is worth explaining them further:

When the instrument, which by definition is subjected to pressure during operation, reaches the defined drilling depth, the stop may slip on meeting a surface inclined with respect to the axis of the instrument or an irregular surface, concave or convex at places (which is very frequently the case in implantology, where dental implants have to be fitted on to an apex of a bone crest only slightly larger in diameter than the implant). The probability of slipping is far from negligible, and is greater in cases where the bone for drilling is very spongy and loose or in the very frequent cases where the uppermost part of the apex of the bone crest (always on the same side as the tongue) is of hard cortical bone whereas the lower part (on the buccal side) is softer (only slightly corticalised). The result of such an eventuality will inevitably be a side slip, i.e. a lateral drift of the drill axis, and a consequently oval hole.

This serious disadvantage of the known devices is one reason for lack of primary stability of the implant.

Techniques and knowledge in implantology are in process of development. One development is towards use of non-traumatic techniques, when preparing holes in bones for receiving "screw implants in root form". Another development is towards adapting drilling techniques to the four bone densities (type D1 comparable to oak wood down to type D4, corresponding to expanded polystyrene) normally found in dental implantology. Consequently the dentist, or more precisely the implantologist, will need a very large number of preferably increasing drill diameters (usually from 1.5 to 5 mm). This is to prevent injury through heating of the dense bone by too rapid drilling of the hole. Another purpose is to adapt the preparatory work to the different diameters of the implants at present available. A final aim, in the case of spongy or loose bone, is to produce holes sufficiently tight for inserting an implant with good primary stability without risk of fracturing the bone trabiculation when inserting an implant, through insufficient drilling of the hole in the bone.

These situations are not taken into account by any of the known safety devices for limiting the depth of drilling.

Finally no citation discloses means for precalibrating the planned depth of drilling and storing the said depth.

SUMMARY OF THE INVENTION

The object of the invention is to reduce the said disadvantages and take account of the considerations stated.

The object is achieved by the device and method defined in the claims.

The claimed stop, in addition to being mobile, can be described as "active" in contrast to the "passive" character of the stops known in the prior art, in that the co-operation as described between the stop and the drilling tool or instrument inevitably and automatically results in withdrawal of the instrument from the hole just made by the practitioner, as soon as the desired depth is reached. The moving stop positioned according to the invention effectively prevents the preset drilling depth from being exceeded, together with any other risks such as ovalisation or lesions.

To sum up, as soon as the stop meets an obstacle and is thus prevented from rotating, the stop moves exclusively in the direction for shortening the length of the exposed working part of the instrument, thus avoiding any accident.

Likewise if, when the instrument is set in rotation, the inertia of the stop causes it to rotate on the co-operating means (the screw and nut system in one example) connecting these two elements (i.e. the stop and the instrument, more particularly a drill or drill bit), the resulting rotation communicated to the stop will involve axial displacement thereof in a direction such that the displacement will shorten the portion of the working part of the tool initially projecting from the stop. This is a safety factor, particularly in dental implantology.

The automatic withdrawal of the drill bit at the end of travel eliminates any risk of drift by the tool, i.e. any risk of ovalisation of the hole due to side-slipping of the stop. This feature, as we have seen, is of fundamental importance in dental implantology, particularly in the case of slightly corticalised bone.

Retraction of the drill bit also prevents any excess drilling during the preparation of a hole in very spongy bone (usually in the posterior part of the jaw bones, particularly the upper jawbone). It is essential to avoid any excessive drilling of the tender bone. The lack of accuracy resulting from excessive drilling will destroy the primary stability of the implant, such stability being essential for incorporation in the bone (i.e. the creation of a stable biological link between the bone and the implant so that it can bear loads efficiently and over a longer period without clinical symptoms. This is a fundamental principle and aim of modern implantology).

The adjustment of the depth of drilling by the prior-art stop devices, using bearings or notches, is rudimentary and insufficiently accurate. By contrast, in the device according to the invention, the stop is connected to the non-operative part (shank) of the instrument, preferably via a micro-screwthread, permitting easy, fine and accurate micrometric adjustment of the depth of drilling.

The advantage of micrometric adjustment, by precalibrating the depth of drilling, using an X-ray or tomographic film to scale 1:1, is that optimum use is made of the depth of bone available, without risk of injury to neighbouring structures. The chosen depth of drilling can be adjusted easily during the operation, by very accurate micrometric movement of the stop, leaving the drill in the bone hole under X-ray monitoring. In the case of digital radiography, the depth can be checked and corrected if required (i.e. the stop can be re-positioned) immediately, with the additional advantage of better use of time. Finally the micro-screwthread is a means of accurately correcting and compensating the error due to prestress of the edge of the stop by the nearest part of the bone surface (the position of a stop is pre-adjusted relative to the drill axis—an impossible operation in the case of a stop with bearings or notches).

This method also has an economic advantage, since the standard diameter of shanks (for different diameters of the working part) of drills used in implantology is always 2.2 millimeters, so that a standard stop can be used for a whole range of drills. In other applications where necessary, the standard stop can be supplemented by stops adapted to other shank diameters. In all cases, the device according to the invention enables the number of stops to be narrowly limited, perhaps to a single standard type covering practically all sizes of drill (a feature which makes these devices all the more advantageous in sectors such as implantology where wear is particularly important).

BRIEF DESCRIPTION OF THE DRAWINGS

An embodiment of the device according to the invention will now be described in detail by way of non-limitative example with reference to the accompanying drawings in which.

DESCRIPTION OF THE PREFERRED EMBODIMENT

An instrument 10, in the present case a drill bit used more particularly in dental surgery (see FIG. 1) has an active or cutting part 11 (i.e. the working part) provided along its length with conventional helical cutting edges (directed towards the right though not shown on the drawing) and with marks or grooves 14 likewise conventional on this kind of drill, with a shank 12 adapted to engage in a chuck or manual component (not shown) for driving the drill in rotation. The rotation is usually directed to the right viewed in the direction from shank to active part (see arrow R in FIG. 1), the edges on the active part being oriented in the same direction. In its front part, the shank 12 has a screwthread over a distance D such that all the usual depths of drilling can be displayed by a stop 20 (see hereinafter). The screwthread 15 is in the opposite direction to the direction of rotation R. In the example shown, therefore, the screwthread is left-handed. It is advantageous to choose a micro-thread or at least a very fine thread for the purpose of micrometric adjustment of the desired drilling depth, as will be seen hereinafter.

Figure 2:
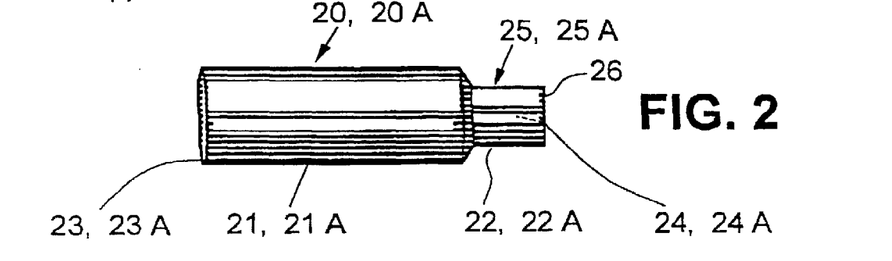
FIG. 2 shows an embodiment of a movable stop.

The component 20 shown in FIG. 2 is a movable stop formed at its rear 22 with an internal screwthread 24 corresponding to the screwthread 15 on the drill 10, the components 22, 24 forming the equivalent of a nut (general reference 25). The nut 25 extends towards the front of a tubular body 21 which partly covers the working part 11. In this embodiment, therefore, the stop 20 has a basically bell shape. The inner diameter of the body 21 is made such that the stop can be fitted on drills of different diameter (the most frequently used varying between 1.5 mm and 5 mm approx.). A standard stop or, if required, two standard stops can thus be designed, one for drills having a working part between 1.5 mm and 3.5 mm in diameter and the other for drills having a working part between 2.5 mm and 5 mm in diameter. These two stops will be sufficient for a device of universal application, since furthermore the shank diameter of most drills used in implantology is uniformly equal to 2.2 mm.

Figure 3:
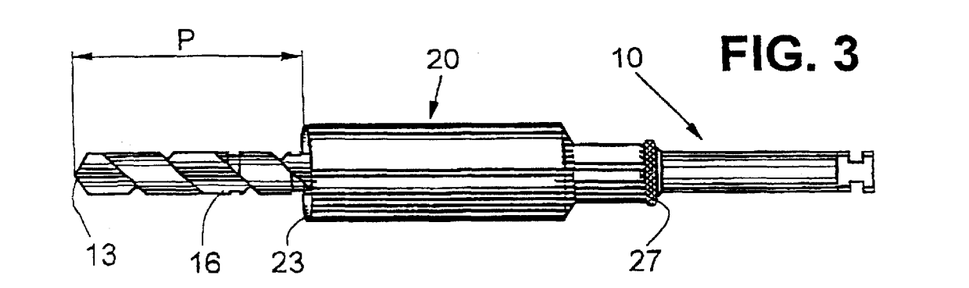
FIGS. 3 and 4 show the safety device when assembled, with the stop in two different positions.

The stop 20 co-operates with the drill 10 mounted on it, like a nut on a screw (screw and nut system 15–25 accompanying or converting movement in rotation into movement in translation and vice versa, more particularly in the sense that when the rotating nut, i.e. the stop 20, is immobilised the screw, i.e. the drill bit 10, continues to rotate but moves longitudinally). The stop 20 can then be finely adjusted by the practitioner, so that the exposed length 16 of the working part 11 between the front surface 23 of the stop and the end part 13 of the working part of the drill 10 will correspond very accurately to a desired depth P for the planned drilling (FIG. 3).

Figure 4:
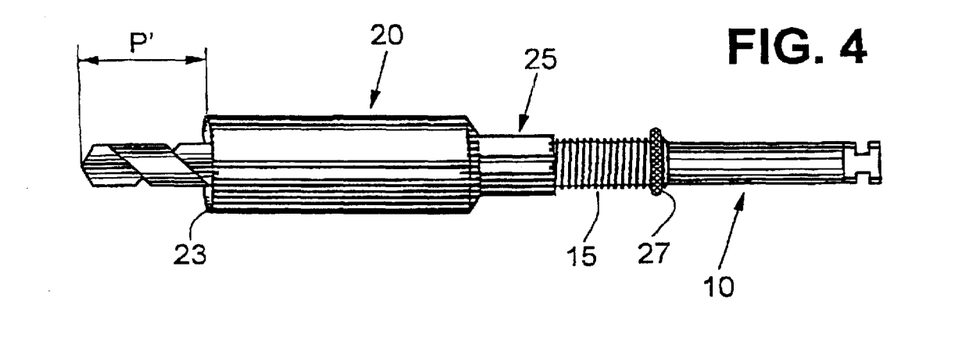

The means of co-operation between the drill 10 and the stop 20, i.e. the screw and nut system 15 and 25 in the example, must be designed so that the frictional forces encountered are just sufficient for the drill 10, when driven in rotation, to entrain the stop 20 without the stop moving in linear manner (the result of a difference between the angular velocity of the stop and that of the drill (relative motion)). The previously-mentioned choice of the nature and kind of the screwthread preferred for this system (micrometric thread), in addition to accurately positioning the stop, serves or at least contributes to satisfying this condition, since the frictional forces must be such that the withdrawal of the drill begins as soon as the stop is immobilised, because the drill comes in contact with neighbouring tissues. Depending on the case, one and/or the other component of the said co-operating means, i.e. the internal thread 24 and/or the thread 15, can be provided with a braking means which increases the frictional forces. Another variant would be to fit a ring or O-ring 27 (FIGS. 3 and 4) against the rear surface 26 of the nut 25 and on the screwthread 15. Of course, any other means known to the skilled man may be used. By way of example, in another variant, the components 15 or 25 can be magnetised or provided with a magnetic chip, to obtain a preset frictional force between the said components.

Figure 7:
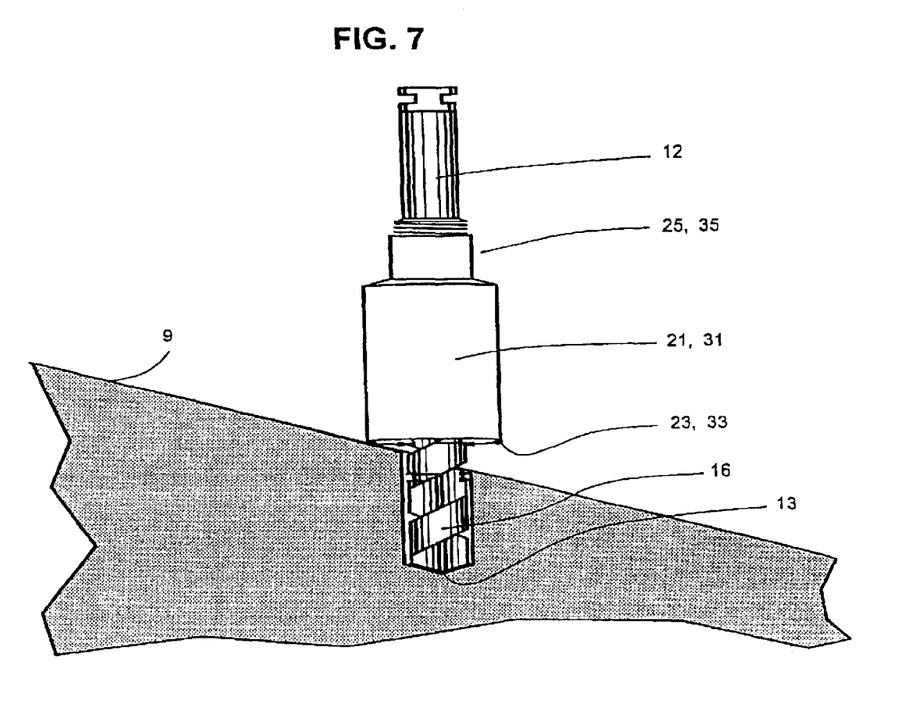
FIG. 7 shows the device in the working phase (end of phase when the stop comes against a diagrammatically indicated wall)

During the operation, when the planned depth of drilling is reached, the front surface 23 of the stop 20 comes against the neighbouring surface 9 (see FIG. 7). The resulting bearing force on the stop 20, as soon as it equals the frictional forces on the connection between the drill 10 and the stop 20, will immobilise the stop 20 and thus retract the drill bit into the tubular body 21 (see FIG. 4, where the portion 16 (equal to P) of the working part 11 (see FIG. 3) has changed to a value P' (FIG. 4) with P'<P, as a result of the immobilisation in conjunction with the rotation of the drill bit).

This reduction is also indicated by the marks 14 on the drill bit if provided thereon (see hereinbefore, introductory part).

Figure 5:
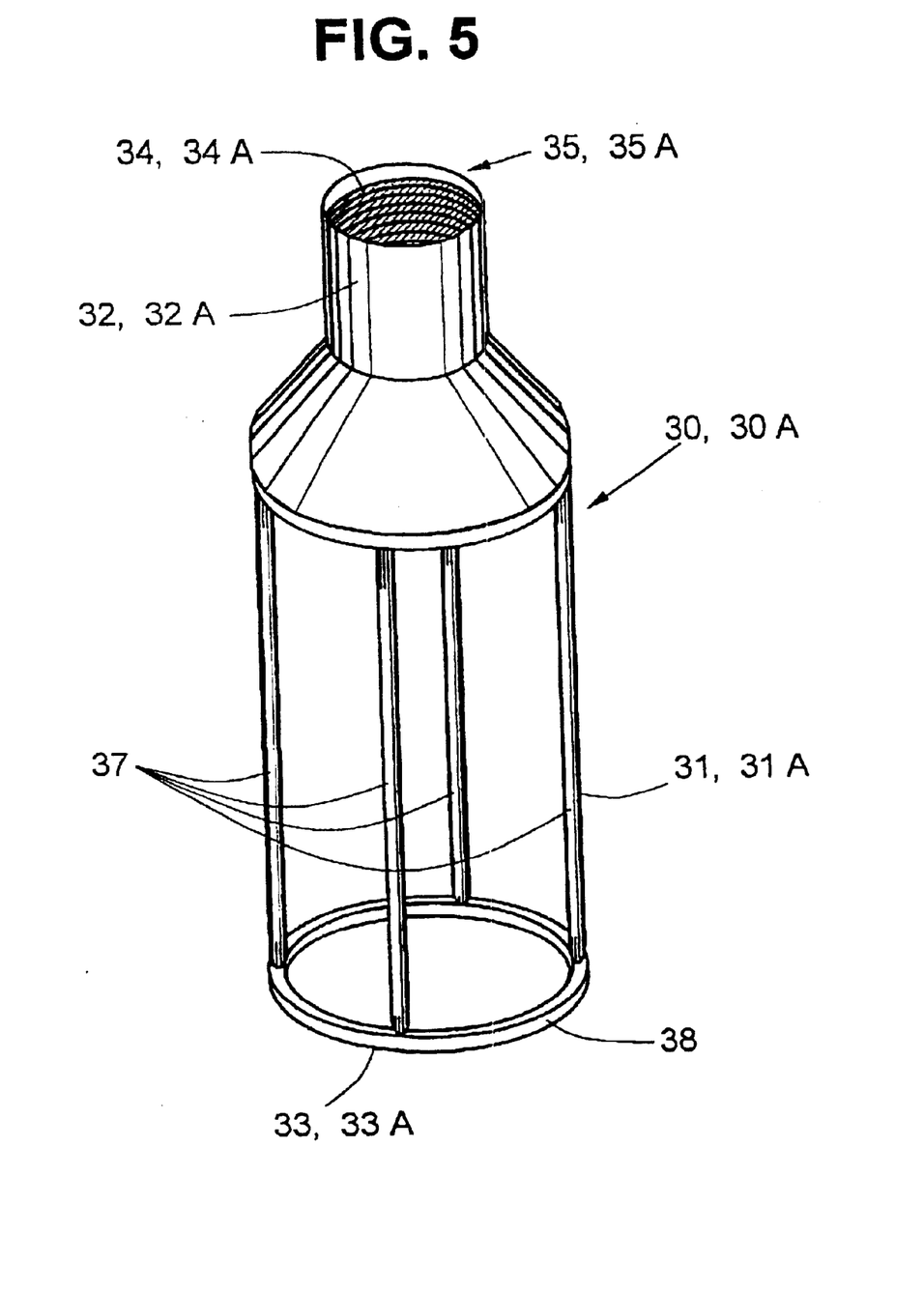
FIG. 5 is a larger-scale view of another embodiment of a movable stop.

The shape and structure of the stop can of course vary. By way of example, FIG. 5 shows a stop 30 with a basket structure. A rear internally threaded part 32, 34 forms a nut 35 and is prolonged by a cylindrical cage 31 comprising a bottom hoop 38 (front surface 33) connected to the nut 35 by four bars 37. This structure does not completely cover the working part 11 of the bit 10, i.e. it leaves this part exposed so that the bit is more efficiently cooled, since a larger surface area of the working part will then be in contact with the cooling liquid. In other respects, this stop of course serves the same purpose as the stop 20; the nut 35 co-operates with the screw 15 on the bit 10, which can be withdrawn into the cage 31 as soon as the front part 33 comes against the neighbouring surface (reference 9 in FIG. 7).

Figure 6A:
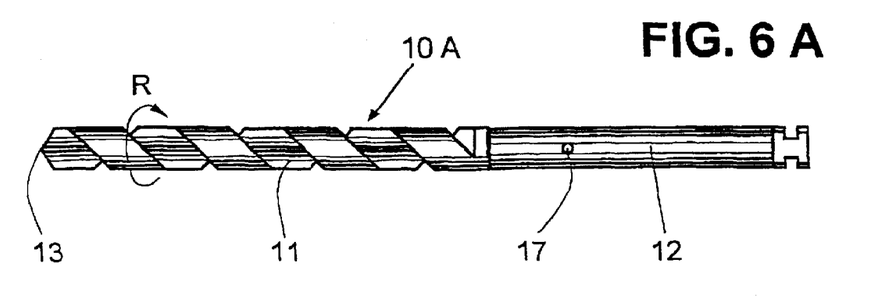
FIG. 6A shows a conventional drill.
Figure 6B:
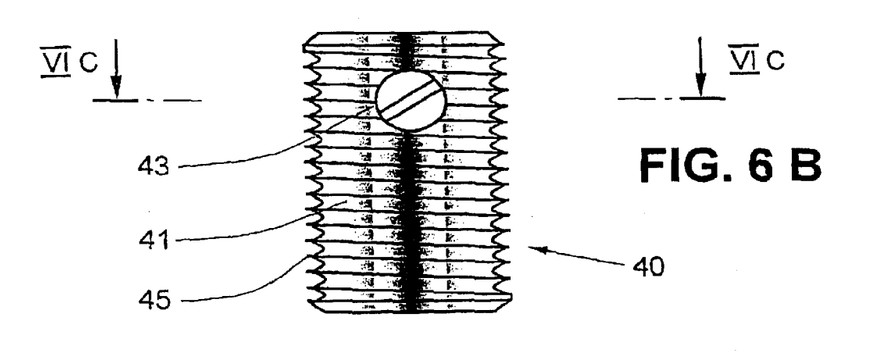
FIG. 6B, on a larger scale, shows an intermediate element for connection and co-operation between the drill and the stop, in one embodiment.
Figure 6C:
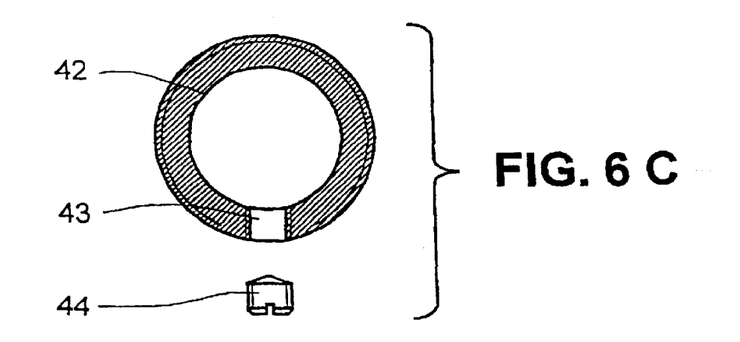
FIG. 6C is a section along line VI C–VI in FIG. 6B.

In a variant embodiment (in which the drill bit and the stop are connected indirectly), the drill bit 10A (see FIG. 6A) is identical in all respects with the bit 10 in FIGS. 1 to 4 except that it has no screwthread 15 (or any other means for converting rotation into axial movement) on the part 12, but only has a hollow 17 at a defined place on the said part. A removable intermediate component, general reference 40 (see FIGS. 6B and 6C, the latter being a section along the line VI C in FIG. 6B) is also provided. The component 40 has the general shape of a sleeve 41 having a given length equivalent to the length D (compare FIG. 1) whereas the diameter of the internal thread 42 is equal to the diameter of the shank 12 (which by definition is not threaded in this variant embodiment). The sleeve 40 has a left-hand screwthread 45. It is adapted to be accurately fitted on the shank 12 at the required place (advantageously corresponding to the position of the screwthread 15 on the bit 10) and to be locked thereon by a locking micro-screw 44 (FIG. 6C) inserted into a screwthreaded hole 43. The end (no reference number) of the locking micro-screw can engage in the hollow 17 in the shank 12 (FIG. 6A; a hollow of this kind can of course easily be made by the practitioner himself on site if the drill shank does not have such a hole). As can be seen, since the component 40 is movable, the device has increased, unrivalled flexibility and usefulness. More particularly, families of sleeves can be provided, all having the same outer diameter and the same screwthread but different internal diameters (depending on the diameters of the drill shanks). For example a single stop 20A, 30A having a body 21A, 31A and a front surface 23A, 33A (see FIGS. 2 and 5) with a nut 25A, 35A formed by the rear part 22A, 32A and having an internal screwthread 24A, 34A corresponding to the screwthread 45, can be used for an entire range of drill bits.

In general, of course, the direct or indirect co-operation between the stop and drill shank can be obtained by any other known means equivalent to those described by way of example, i.e. adapted to convert movement in translation into movement in rotation and vice versa (e.g. one or more helical grooves and balls).

In addition to the accuracy of operation by the device according to the invention, any risk of exceeding the previously-determined depth and any consequent risk of ovalisation of the hole and injury to the tissues are completely excluded.

Owing to its flexibility and general usefulness, the safety device according to the invention also has a considerable financial advantage over the known fixed-stop safety devices. As already stated, it will be sufficient for the specialised practitioner to obtain a single kind of stop (standard stop) e.g. in dental implantology, where the diameter of drill bits is uniformly 2.2 mm. In other cases, the user will need only a very limited number of different stops, depending on the application. In all cases there will be no need to keep a stock of drills with fixed stops corresponding to different depths.

Also the bodies 21; 21A; 31; 31A of the stops 20; 20A; 31; 31A can be made of any sterilisable opaque or transparent material.

Figure 8:
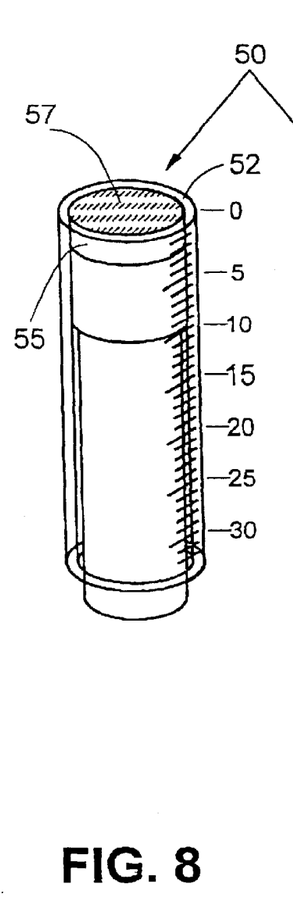
FIGS. 8, 9 and 10 show the device for precalibrating and storing the depth of drilling.
Figure 9:
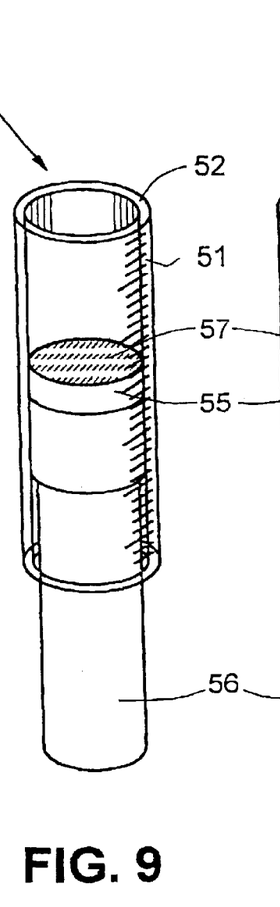
Figure 10:
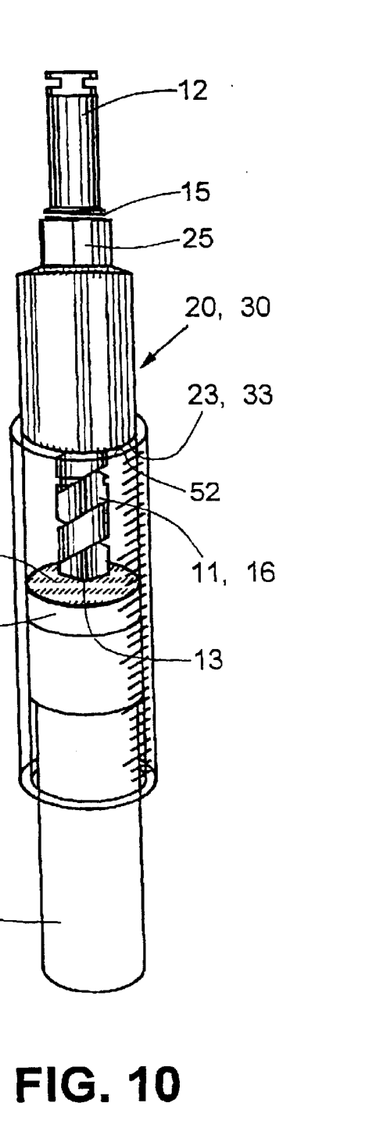

As can be seen, the chosen micrometric screwthread enables the defined drilling depth to be very finely adjusted. On the one hand the distance, i.e. the depth between the end point of the bit and the front surface of the stop, can be measured in various ways. On the other hand, it may be advantageous to pre-calibrate the detailed depths of drilling for a number of implants and store them during an operation. To this end, a set of specially designed gauges are provided and can be disposed in a suitable block or box and used in a process described hereinafter. Each gauge 50 (see FIGS. 8, 9 and 10) comprises a cylinder 51 graduated in millimeters (e.g. from zero to 30 mm), made of transparent material sterilisable in an autoclave or a chemiclave, containing a piston 55 (with upper surface reference 57), preferably provided with a piston rod 56 for easy resetting to zero. The 0 mm mark is flush with the top surface 52 of the cylinder 51. The outer diameter of the cylinder 51 is approximately equal to the outer diameter of the stop 20; 30, so that the front surface 23, 33 of the stop 20, 30 can come exactly against the top part 52 of the gauge (see FIG. 10). In a first step, the upper surface 57 of the piston 55 is opposite the zero mark (FIG. 8). In a second step, the practitioner places the end 13 of the working part 11 of the bit against the piston 55, thus driving it into the cylinder body until the piston surface 57 is level with the mark corresponding to the planned depth of drilling (e.g. 15 mm, see FIG. 10). He then acts on the stop by rotating it until the front surface 23, 33 thereof comes against the edge 52 of the cylinder; the stop is in position for the planned drilling operation, as regards the displayed depth. Depending on the situation, i.e. when the practitioner intends to drill a number of holes, it appears advantageous to pre-calibrate and store the choice of the various depths. To this end, the practitioner will use as many gauges as planned depths, a particularly interesting idea when a number of dental implants are fixed on the same patient during the same treatment session.

What is claimed is:

1. A safety device comprising:
    a stop for a rotary drilling instrument, the stop being movable on a rotary drilling instrument to a position corresponding to a desired drilling depth of the rotary drilling instrument to prevent exceeding the desired drilling depth; and
    means for converting rotary motion of the rotary drilling instrument to relative motion between the stop and the rotary drilling instrument to cause the drilling instrument to withdraw to the rear relative to the direction of drilling by action of said means as soon as a front part of the stop comes in contact with a surface.

2. The safety device according to claim 1, wherein the means for converting comprises a nut and screw, the direction of threads of the nut and screw being opposite to the direction of rotation of the drill in operation.

3. The safety device according to claim 2, wherein the screw comprises a screwthread on a shank of the rotary drilling instrument and the nut comprises a corresponding internal thread of a rear part of the stop.

4. A The safety device according to claim 2, wherein the screw comprises an intermediate element in the form of a sleeve with a body that is externally screw-threaded, said intermediate element being adapted to be fitted on a shank of the rotary drilling instrument, and the nut comprises a corresponding internal thread of a rear part of the stop.

5. The safety device according to claim 1, wherein the stop has a body that extends at least partly around the drilling instrument, the desired drilling depth corresponding to a portion of the drilling instrument projecting from the front part of the stop, the desired drilling depth being pre-adjustable by action of the converting means, and the length of the portion decreasing when the front part comes in contact with the surface.

6. The safety device according to claim 1, wherein the stop comprises a body that is one of a tubular solid and an openwork cage.

7. The safety device according to claim 6, wherein the body is made of a sterilisable, opaque or transparent material.

8. The safety device according to claim 6, wherein the converting means comprise a braking element.

9. The safety device according to claim 1, further comprising a gauge in the form of a transparent graduated body and a piston, an upper surface of the graduated body corresponding to a zero mark on a scale on the graduated body and wherein an outer diameter of the graduated body is approximately equal to an outer diameter of the stop so that the front part of the stop contacts an upper surface of the graduated body when the graduated body is mated with the stop.

10. A method of precalibrating and storing desired drilling depth using the safety device according to claim 9, comprising the steps of pressing the front part of the stop against the upper surface of the graduated body and driving the piston inside the graduated body by action of the converting means, the action resulting in a thrust exerted on the piston by the rotary drilling instrument until an upper surface of the piston is opposite a graduation mark corresponding to the desired drilling depth.

11. A safety device comprising:
    a drill having an operating bit at one end thereof and an external screw thread on a shank thereof, said external screw thread being wound in a first direction that is opposite to a second direction of operation of said drill;
    a stop coaxial with said drill and having a rear end with an internal screw thread that mates with said external screw thread of said drill and a front end that engages a work surface during operation of the device, said stop being movable longitudinally along said drill by rotating said stop; and
    said internal and external screw threads having a frictional engagement that overcomes an inertia of said stop to cause said stop to rotate in the second direction with said drill when said drill is rotating in the second direction and said front end of said stop is not engaging a work surface, the frictional engagement being overpowered by engagement of said front end of said stop with a work surface to cause said stop to rotate relative to said drill and move toward said operating bit.

* * * * *

UNITED STATES PATENT AND TRADEMARK OFFICE
CERTIFICATE OF CORRECTION

PATENT NO. : 6,739,872 B1
DATED : May 25, 2004
INVENTOR(S) : Turri

It is certified that error appears in the above-identified patent and that said Letters Patent is hereby corrected as shown below:

Column 8,
Line 3, change "A The" to -- The --.

Signed and Sealed this

Tenth Day of August, 2004

JON W. DUDAS
*Acting Director of the United States Patent and Trademark Office*